United States Patent [19]

Dougherty

[11] Patent Number: 4,995,879
[45] Date of Patent: Feb. 26, 1991

[54] INTRAOCULAR LENS WITH UNITARY DRAWN HAPTICS

[76] Inventor: Robert R. Dougherty, 830 Greenridge Dr., La Canada, Calif. 91011

[21] Appl. No.: 419,127

[22] Filed: Oct. 10, 1989

[51] Int. Cl.$^5$ .............................................. A61F 2/16
[52] U.S. Cl. ...................................................... 623/6
[58] Field of Search ............................................ 623/6

[56] References Cited

U.S. PATENT DOCUMENTS

| | | | |
|---|---|---|---|
| 4,174,543 | 11/1979 | Kelman | 623/6 |
| 4,280,232 | 7/1981 | Hummel | 623/6 |
| 4,439,873 | 4/1984 | Poler | 623/6 |
| 4,813,956 | 3/1989 | Gupta | 623/6 |

Primary Examiner—Randall L. Green
Assistant Examiner—David H. Willse
Attorney, Agent, or Firm—Kelly Bauersfeld & Lowry

[57] ABSTRACT

An improved intraocular lens and related method of production are provided, wherein resilient drawn haptics are formed integrally with a lens body for supporting the lens body at a centered position with a patient's eye. A lens preform is constructed from a selected polymeric material to include the lens body having integrally formed lobes at selected points on the periphery thereof. The lobes are then drawn outwardly under elevated temperature conditions and set with a selected curvature to form resilient, substantially filamentary haptics or support loops of a desired shape. Such drawing of the polymeric material results in substantial alignment of polymers longitudinally along the haptics such that the haptics exhibit a combination of significant resiliency and high structural strength.

11 Claims, 1 Drawing Sheet

INTRAOCULAR LENS WITH UNITARY DRAWN HAPTICS

BACKGROUND OF THE INVENTION

This invention relates generally to intraocular lenses designed for surgical implantation into the eye as a replacement for a removed natural lens. More specifically, this invention relates to an improved intraocular lens having a preferred unitary or one-piece construction and a related production method, wherein the one-piece lens includes resilient support haptics having improved structural properties.

Intraocular lenses in general are well known for implantation into the eye as a replacement for a natural crystalline lens which has been removed surgically due to a cataract condition, injury, or the like. Such intraocular lenses are typically constructed from a selected transparent and relatively inert plastic material, such as polymethylmethacrylate, to form a lens body of generally disk-shaped configuration with optical characteristics approximately a natural lens. Support structures known commonly as haptics project outwardly from the lens body for contacting adjacent tissue structures within the eye, for purposes of maintaining the lens body in generally aligned relation with the iris and pupil. In some intraocular lens styles, the lens body and related haptics are designed for implantation into the so-called anterior chamber of the eye in front of the iris and pupil, whereas other common lens designs are intended for implantation into the so-called posterior chamber behind the iris and pupil.

Significant design activity has focused upon the haptic support structures in an effort to provide improved biocompatibility within the eye, in combination with sufficient structural strength for reliable support of the lens body while avoiding discomfort attributable to irritation of delicate eye tissues. In this regard, for substantially optimized biocompatibility when implanted into humans, it is generally desirable to form the haptic structures from the same inert plastic material used to form the transparent lens body. The prior art thus includes many examples of unitary or one-piece intraocular lenses having haptic structures of many different specific geometries which are formed by casting or machining to be integral with a lens body. See, for example, U.S. Pat. Nos. 4,687,485; 4,190,049; and 4,134,161. However, these integrally formed haptics have generally required relatively complex and costly manufacturing operations. Moreover, these integral haptics generally do not exhibit sufficient resiliency to avoid undesirable tissue irritation, since manufacturing limitations normally require such one-piece haptics to have relatively large cross-sectional dimensions to provide satisfactory tensile strength.

Alternative haptic support structures have been fashioned from filamentary material such as polypropylene or the like for separate mounted attachment onto a lens body. Such filament haptics typically have an inboard end adapted for physical anchoring within a small counterbored seat formed in the periphery of a lens body, in combination with an outboard support loop having an outwardly convex curvature for contacting eye tissue. While filamentary material beneficially possesses improved resiliency without significantly compromising structural integrity, the formation and assembly of filament haptics to lens bodies involves additional and relatively tedious manufacturing steps. In addition, the resultant intraocular lens includes multiple materials and thus is not preferred by many surgeons.

There exists, therefore, a significant need for further improvements to intraocular lenses, particularly with respect to providing a lens having integrally formed haptic support structures possessing relatively high resiliency together with high structural strength. The present invention fulfills these needs and provides further related advantages.

SUMMARY OF THE INVENTION

In accordance with the invention, an improved intraocular lens is provided for surgical implantation into the eye, wherein the lens includes a transparent lens body formed integrally with support haptics having a combination of relatively high resiliency and strength characteristics. The integral support haptics are formed by drawing polymeric material directly and integrally from the periphery of the lens body to obtain filamentary loop haptics having substantial longitudinal orientation of polymers.

In a preferred form of the invention, a lens preform is formed as by machining or casting from a selected and relatively inert plastic material, such as polymethylmethacrylate or the like used in the intraocular lens industry. The lens preform includes a lens body of generally disk shape and selected optical characteristics, together with relatively small outwardly protruding lobes formed integrally at selected points on the periphery of the lens body. These lobes are subjected to localized heating in a manner preferably avoiding optical distortion of the lens body, whereupon the lobes are grasped by an appropriate tool and drawn outwardly from the lens body. This drawing step effectively reduces each lobe to a relatively thin filamentary support loop having substantial alignment of polymers to extend in parallel with a longitudinal axis of the support loop. The support loop is further set with a selected curved geometry, such as by displacing the drawn loop over a controlled temperature template, to produce a highly resilient support loop haptic having high structural strength characteristics.

In one alternative form of the invention, the lobes can be adapted to receive a selected pigment material which can be codrawn with the lobe to provide a support loop of selected color. In another form, the lobes can be shaped in complex curved geometries adapted for drawing of a limited region thereof, resulting in a support loop having a limited inboard segment of high flexibility, and an outboard segment of selected shape for contacting eye tissue.

Other features and advantages of the present invention will become apparent from the following detailed description, taken in conjunction with the accompanying drawings which, illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
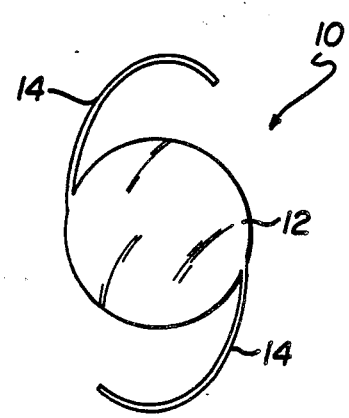
FIG. 1 is a front elevational view depicting an intraocular lens constructed according to the novel features of the invention.

As shown in the exemplary drawings, an improved intraocular lens is referred to generally in FIG. 1 by the reference numeral 10, wherein the lens has a one-piece or unitary construction including a transparent lens body 12 with outwardly extending curved resilient support loop haptics 14. In accordance with the invention, these support loop haptics 14 are formed by drawing in an outward direction from the lens body to obtain substantial alignment of polymers longitudinally along the support loops, resulting in a highly desirable combination of physical characteristics including relatively high structural and tensile strength with high resiliency.

Figure 2:
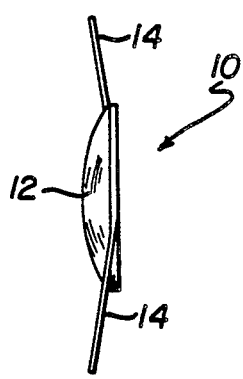
FIG. 2 is a side elevational view of the lens shown in FIG. 1.

FIGS. 1 and 2 illustrate an exemplary intraocular lens 10 formed according to the invention, for implantation into the eye as a replacement for a cataractous or otherwise disfunctional natural crystalline lens. The lens 10 includes the lens body 12 which is formed typically from a cast and/or machined transparent plastic material having selected optical grade characteristics. One common plastic material used in the production of intraocular lenses is polymethylmethacrylate, although other materials such as polysulfone, polycarbonate, etc. can be used. The lens body 12 is shaped to provide a selected set of optical characteristics typically simulating those found in a normal natural lens, with the accompanying drawings (FIG. 2) showing the lens body with convex and generally planar anterior and posterior surfaces, respectively.

The support haptics 14 extend outwardly from the lens body 12 to support and center the lens body within a patient'eye (not shown) at a position corresponding to a normal line of sight. Accordingly, the support haptics 14 contact adjacent tissue within the eye to maintain the lens body in the desired position. In some lens designs, the support haptics contact the peripheral junction region between the iris and the cornea when the lens is implanted within the so-called anterior chamber in front of the iris. In other lens designs, the support haptics contact the ciliary sulcus region and/or are seated within the capsular bag when the lens is implanted into the so-called posterior chamber behind the iris. Such implantation techniques and procedures are well known in the art and thus are not further described herein.

Regardless of the chamber of lens implantation, it is important for the support haptics 14 to contact the adjacent delicate eye tissue in a manner which avoids irritation discomfort and/or trauma. In this regard, the haptics 14 are traditionally formed with a high degree of flexibility or resiliency, and are shaped with smoothly curved outer surfaces to provide gentle supportive contact with eye tissue. FIG. 1 illustrates the support loop type haptics extending outwardly and generally tangentially from opposite sides of the lens body and then curving with a relatively conventional geometry through an outwardly convex region for generally tangential seating against eye tissue. FIG. 2 depicts the loops with a component of anterior angulation for purposes of spacing the lens body 12 posteriorly from the pupil when the lens is implanted into the posterior chamber.

In accordance with primary aspects of the invention, the support loops 14 have a thin filamentary construction to possess a high degree of desirable resilience. However, unlike filament support loop haptics used in the prior art which are separately manufactured for mount-on assembly with a lens body, the present invention forms the filamentary haptics 14 integrally with the lens body 12. Importantly, the integral support haptics 14 are produced by a longitudinal drawing process which substantially aligns elongated polymer molecules in a direction extending longitudinally along the lengths of the loops, thereby achieving high structural shear and tensile strength without impairing the desired high flexibility.

Figure 3:
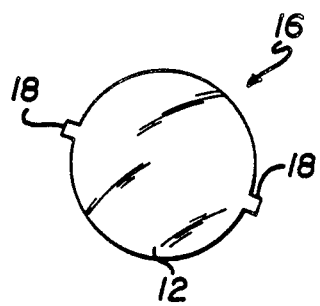
FIG. 3 is a front elevational view of an exemplary lens preform.

The improved intraocular lens 10 is formed from a preform 16 shown in FIG. 3. This preform 16 includes the lens body 12 which may be substantially in finished form or, alternately, in a blank form adapted for later shape processing to the desired set of optical characteristics. The preform 16 additionally includes a plurality of two or more integrally formed lobes 18 at selected points around the periphery of the lens body, wherein these lobes are designed for drawing into the shapes of the final support loop haptics.

Figure 4:
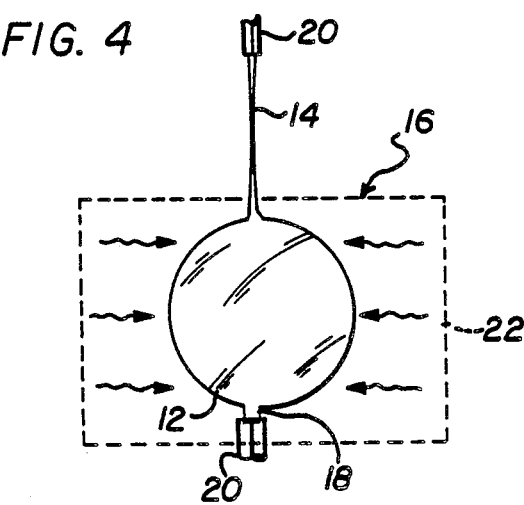
FIG. 4 is a somewhat schematic view showing the step of drawing an integral support loop haptic from the preform of FIG. 3.
Figure 5:
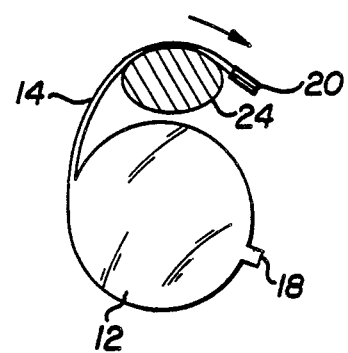
FIG. 5 is a somewhat schematic view illustrating shaping of the drawn support haptic into a curved contour.

FIG. 4 illustrates the lens preform 16 subjected to a drawing step. More specifically, the lobes 18 are heated by means of an appropriate heat source to a suitable temperature at which the lens material can be drawn. One or more tools 20 are provided to grasp the lobes 18 one at a time or simultaneously while in the heated state, and to pull outwardly to draw each lobe into an outwardly extending filament-like support loop 14. Suitable support structures (not shown) are provided to hold the lens body in place during this drawing step or steps. This drawing step is performed concurrently with or followed by a loop shaping step during which the drawn support loop is turned relative to the lens body 12 to the final outwardly convex geometry. FIG. 5 illustrates this shaping step to include wrapping of the drawn loop over a contoured mandrel 24 or the like, wherein the mandrel may be preheated for obtaining thermal set. The outboard ends of the thus-drawn support loops 14 can be trimmed to the desired final length.

A variety of different processing equipment may be used to perform the drawing and shaping steps depicted in FIGS. 4 and 5. For example, with reference to FIG. 4, various heat sources may be used to apply heat to the lens sufficient to permit drawing of the lobes 18, while avoiding undesired surface distortion of the lens body. A heated bath 22 may be used for this purpose. Alternately, a laser heat source may be used to apply heat energy to the lobes, substantially without heating the lens body 12, with a suitable heat sink being provided to dissipate excess heat from the lens body, if desired. Other types of conductive, convective, microwave, ultrasound, etc. heat sources may also be used. Moreover, if desired, the heating step may take place within an oxygen free atmosphere to avoid oxidizing the plastic lens material.

The drawn support loop haptics 14 can be formed with a small filamentary cross sectional size similar to the separately mounted filament loops of the prior art, but without altering the integral connection between the haptics and the lens body 12. These thin loop haptics beneficially exhibit extremely high flexibility for resiliently and comfortably supporting the lens body within a patient's eye. However, the step of longitudinally drawing these loops also rearranges the randomly oriented polymer molecules within the lobes 18 into substantial axial alignment extending linearly along the support loops. This orientation of polymers provides the loops with high structural shear and tensile strength.

Figure 6:
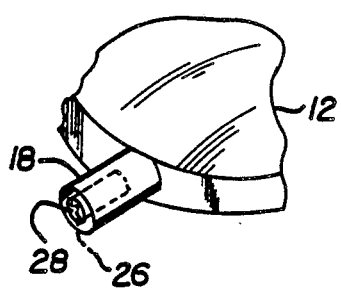
FIG. 6 is a fragmented perspective view illustrating an alternative lens preform construction.

A variety of alternative intraocular lens geometries can be formed utilizing the concepts of the present invention. For example, as viewed in FIG. 6, the lobes 18 can be formed with cast or drilled recessed seats 26. These seats 26 are outwardly open for reception of a small quantity or plug of a selected pigmented material 28 in the event that colored support haptics are desired for easier visibility during implantation and subsequent clinical analysis. In this regard, the pigmented material may comprise a selected pigment material such as a blue copper thalocyanine which is preferably used to color a small plug of polymeric material of a type compatible and codrawable (FIGS. 4 and 5) with the lobe 18 to provide filamentary support haptics having blue interior lining.

Figure 7:
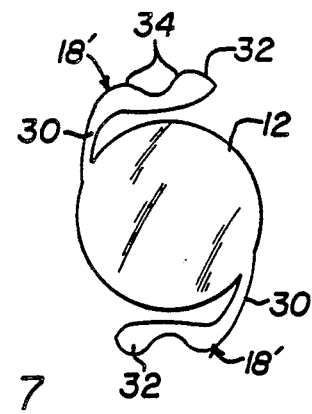
FIG. 7 is a front elevational view of still another alternative lens preform.
Figure 8:
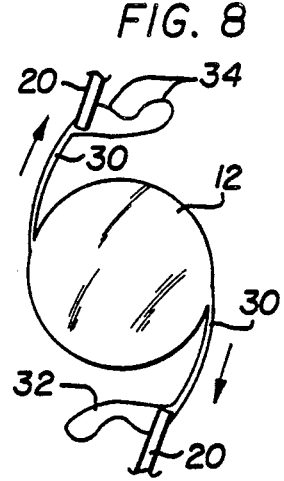
FIG. 8 is a front elevational view similar to FIG. 7 but illustrating the step of drawing integral support loop haptics.

A further alternative lens version is depicted in FIGS. 7 and 8, wherein modified lobes 18' are formed on a lens body 12 (FIG. 7). These modified lobes 18' include inboard segments 30 formed integrally with a lens body 12, and outboard segments 32 having a complex contoured shape to include, for example, a pair of outwardly convex curved seat surfaces 34 for contacting eye tissue. These lobes 18' are drawn as previously desired by grasping the lobes with a tool 20 or the like generally at a juncture between the inboard and outboard segments 30 and 32. With this approach, the inboard segments 30 are drawn outwardly (FIG. 8) to provide inboard regions of high strength and high flexibility, whereas the outboard regions 34 remain undrawn and define broad surfaces for contacting adjacent eye tissue. Of course, in accordance with lobe shape, the lobe material can be drawn additionally at alternative locations, such as between the curved seat surfaces 34, if desired.

Still further modifications and improvements to the invention will be apparent to those skilled in the art. For example, the lobes or other portions to be drawn may be formed with a variety of different cross-sectional shapes according to the particular application, such as a rectangular shape having a long dimension in the fore-aft direction to provide drawn haptics having increased stiffness in the fore-aft direction. Accordingly, no limitation on the invention is intended by way of the foregoing description and the accompanying drawings, except as set forth in the appended claims.

What is claimed is:

1. An intraocular lens, comprising:
   a lens body formed from a selected polymeric material and having selected optical characteristics; and
   at least one elongated support haptic formed integrally with said lens body and extending outwardly therefrom, said support haptic having substantial alignment of polymers longitudinally along at least a portion of the length thereof.

2. The intraocular lens of claim 1 wherein said support haptic comprises a drawn haptic.

3. The intraocular lens of claim 1 wherein said at least one support haptic comprises a plurality of support haptics.

4. The intraocular lens of claim 1 further including a selected pigment material for coloring said support haptic.

5. An intraocular lens preform, comprising:
   a lens body formed from a selected polymeric material and adapted to include selected optical characteristics; and
   at least one lobe formed integrally with and protruding outwardly from said lens body, said lobe having a size and shape for outward drawing into the form of a support haptic;
   said lobe having an outwardly open recessed seat formed therein, and further including a pigment material received into said recessed seat.

6. A method of forming an intraocular lens, comprising the steps of:
   forming a lens preform from a polymeric material to include a lens body adapted for shaping with selected optical characteristics and at least one lobe formed integrally with the lens body and protruding outwardly therefrom; and
   drawing at least a portion of the lobe into the shape of a support haptic.

7. The method of claim 6 wherein said forming step includes forming a plurality of lobes on the lens body, and wherein said drawing step includes drawing each of the lobes to form a plurality of support haptics.

8. The method of claim 6 further including the step of heating the lobe to a draw temperature prior to said drawing step.

9. The method of claim 6 wherein said drawing step further includes shaping the support haptic to have a generally outwardly convex curvature.

10. The method of claim 6 wherein said drawing step includes codrawing the lobe with a selected pigment material.

11. The method of claim 6 wherein said drawing step comprises drawing an inboard end segment of the lobe.

* * * * *